United States Patent [19]

Baudouin et al.

[11] 4,247,720

[45] Jan. 27, 1981

[54] PROCESS FOR PREPARING -TRIMETHYLHYDROQUINONE

[75] Inventors: Michel M. Baudouin, Saint-Fons; Robert M. Perron, Charly, both of France

[73] Assignee: Rhone-Poulenc Industries, Paris, France

[21] Appl. No.: 731,353

[22] Filed: Oct. 12, 1976

[30] Foreign Application Priority Data

Oct. 14, 1975 [FR] France ............................ 75 31950

[51] Int. Cl.$^3$ ............................................ C07C 37/07
[52] U.S. Cl. ................................................ 568/772
[58] Field of Search .......... 260/621 H, 621 D, 621 R, 260/625; 252/463; 568/772

[56] References Cited

U.S. PATENT DOCUMENTS

| | | | |
|---|---|---|---|
| 2,640,084 | 5/1953 | Chitwood et al. | 260/621 H |
| 3,580,970 | 11/1967 | Swift | 260/621 H |
| 3,627,833 | 12/1971 | Tobias | 260/586 R |
| 3,801,651 | 4/1974 | Adolphen et al. | 260/613 D |
| 3,953,526 | 4/1976 | Rosenthal | 568/772 |
| 4,024,196 | 5/1977 | Krekeler et al. | 260/621 H |

*Primary Examiner*—Warren B. Lone
*Attorney, Agent, or Firm*—Burns, Doane, Swecker & Mathis

[57] ABSTRACT

A process for preparing -trimethylhydroquinone by contacting 3,5,5-trimethyl-2-cyclohexene-1,4-dione with an acid catalyst in the vapor phase.

8 Claims, No Drawings

PROCESS FOR PREPARING -TRIMETHYLHYDROQUINONE

BACKGROUND OF THE INVENTION

1. Field of the Invention

The present invention is a process for obtaining trimethylhydroquinone by aromatizing 3,5,5-trimethyl-2-cyclohexene-1,4-dione.

2. Description of the Prior Art

Trimethylhydroquinone is a commercially important chemical compound. For example, it is used as an antioxidant for oil and fatty compounds, as an ultraviolet absorber for plastics and rubber, and as an intermediate for the preparation of medicines such as vitamin E ($\alpha$-tocopherol).

It has been known to synthesize trimethylhydroquinone by reacting 3,5,5-trimethyl-2-cyclohexene-1,4-dione with an acylating agent, usually an anhydride of carboxylic acid, in the presence of an acid catalyst, then subjecting the resulting diester to basic or acid hydrolysis in order to liberate the trimethylhydroquinone. Such a process is described in German application publication No. 2 149 159. From a production standpoint, the prior art process has several drawbacks. The prior art process on an industrial scale involves the handling, use and replenishment of several reagents in a multi-stage operation, requiring the control of different operating conditions which make continuous processing more complicated and increase the overall production costs. Therefore, there exists a need in the chemical process industry to find a simple and economic process for the preparation of trimethylhydroquinone.

SUMMARY OF THE INVENTION

It has now been surprisingly found that the present invention provides a simple and economic process for the preparation of trimethylhydroquinone in high purity and good yields. The process comprises contacting 3,5,5-trimethyl-2-cyclohexene-1,4-dione with an acid catalyst in the vapor phase. The reaction temperature is in the range of from 200° and 600° C. and more preferably between 400° and 500° C. The reaction can be effected at atmospheric pressure or elevated pressures.

It is an object of this invention to provide a new and novel method for economically producing trimethylhydroquinone.

Another object of this invention is to provide a process for the preparation of trimethylhydroquinone which eliminates the need for additional chemical reagents.

It is yet another object of this invention to provide a process which produces a trimethylhydroquinone in high purity and good yields.

Other objects and advantages will become apparent from the detailed description presented herein.

DESCRIPTION OF THE PREFERRED EMBODIMENTS

Broadly, the process of this invention comprises charging the acid catalyst into the reaction with an inert gas or hydrogen, maintaining the reaction zone at reaction temperatures, injecting 3,5,5-trimethyl-2-cyclohexene-1,4-dione into the reaction zone, totally vaporizing the 3,5,5-trimethyl-2-cyclohexene-1,4-dione, mixing the vaporized 3,5,5-trimethyl-2-cyclohexene-1,4-dione with the inert gas or hydrogen, forming a gaseous mixture and contacting the gaseous mixture with the acid catalyst in the vapor phase, at the completion of the reaction, recovering the reaction mixture, and separating trimethylhydroquinone from the reaction mixture.

Process conditions include a reaction temperature of between 200° and 600° C. and preferably between 400° and 500° C. The reaction is conducted in a hydrogen atmosphere or in an inert gas atmosphere such as nitrogen, argon, or xenon. The reaction can be effected at atmospheric or elevated pressures. The elevated pressures can be adjusted by hydrogen or the gases which are inert under the reaction conditions. Generally operating pressures range from 1 to 20 bars and preferably from 1 to 10 bars. The proportion of 3,5,5-trimethyl-2-cyclohexene-1,4-dione in the reaction zone can vary over a wide range and generally represents 1 to 50 volume percent of the gaseous mixture. The apparent time of contact ranges between 0.01 and 50 seconds and preferably between 0.1 and 10 seconds. The apparent time of contact of the gaseous mixture with the catalyst is defined as the length of time in seconds during which one volume unit of the gaseous mixture under the pressure and temperature conditions of the reaction is in contact with an apparent volume unit of the catalyst. The reaction can be carried out continuously or batchwise.

The catalysts which are useful in this vapor phase reaction are acid catalysts which are solids. The acids according to this invention encompass both BRØNSTED and LEWIS definitions. According to Brønsted and acid is any substance that loses a proton. The Lewis concept of an acid is any substance that is an electron acceptor, e.g., any atom that can expand its outer valence shell. The acid catalysts used according to this invention here are those normally employed for heterogeneous catalysis.

As catalysts, the metal oxides from Groups IIa, IIb, IIIa, IVb, Vb, VIb, VIIb and VIII of the Periodic Table of Elements (Handbook of Chemistry and Physics, 51st edition, 1970–71) are used, alone, in mixtures or in combinations. More specific examples include oxides, of beryllium, magnesium, zinc, aluminum, cerium, thorium, uranium, titanium, zirconium, vanadium, niobium, tantalum, chromium, molybdenum, tungsten, maganese, iron, cobalt, and nickel. Adjuvants such as the metalloid oxides (e.g., phosphorous, silicon) may be added to these metal oxides.

The following are specific examples of catalysts: Metal oxides: beryllium oxide (BeO); alumina ($Al_2O_3$); cerium oxide ($CeO_2$); thorium oxide ($ThO_2$); titanium oxide ($TiO_2$); vanadium oxides ($V_2O_5$ - $V_2O_4$); chromium oxide ($Cr_2O_3$); tungsten oxide ($WO_3$). Combinations of metal oxides: $Al_2O_3$ and $Cr_2O_3$; $Al_2O_3$ and $Fe_2O_3$; $Al_2O_3$ and CoO; $Al_2O_3$ and MnO: $Al_2O_3$ and $Mo_2O_3$; $Al_2O_3$ and $V_2O_3$; $Cr_2O_3$ and $Fe_2O_3$. Combinations of metal and metalloid oxides: silica-alumina; silica-magnesia; $TiO_2$ with silica; $ThO_2$ with silica-alumina; MgO with silica-alumina; $Cr_2O_3$ with silica-alumina; $WO_3$ with silica-alumina; $ZrO_2$ with silica-alumina.

Other solid acid catalysts which are suitable include: natural alumina silicates such as kaolinite, montmorillonite or attapulgite; natural zeolites such as chabazite, analcite, heulandite, natrolite, stilbite, thomsonite; synthetic zeolites such as the X, Y zeolites of the faujasite type, L zeolite and Z zeolite analogous to natural mordenite.

The aforementioned catalysts may be activated by acid treatment to increase their effectiveness. Such treatment involves the use of chlorhydric, flurohydric, fluorsilicic acids, and boron fluoride possibly activated with fluorhydric acid. One or more of the noble metals of Group VIII may also be deposited on these catalysts, treated or untreated such as platinum, palladium, rhodium, ruthenium, osmium or iridium. It should be noted that when a natural or synthetic zeolite is used, the activation treatment consists in exchanging the cations deriving from the alkaline metals contained in the zeolite for ions such as $H^+$ or $NH_4^+$, or the cations deriving from polyvalent metals, especially alkaline-earth metals and rare earths, then after the exchange, subjecting the zeolite to thermal treatment.

A class of catalysts, which is particularly preferred according to this invention, comprises alumina alone or alumina in combination with silica or alumina in combination with a metal oxide selected from Groups IIa, IIb, IIIa, IIIb, IVb, Vb, VIb, VIIb, VIII of the Periodic Table, optionally supplemented with silica, a natural alumina silicate, a natural or synthetic zeolite. Equally preferred are silica-magnesia combinations. These catalysts may undergo an acid activation treatment such as described above. More specifically, the catalysts preferably used to effect the vapor phase process of this invention are alumina, silica-alumina, alumina or silica-alumina having undergone acid treatment and/or on which platinum or palladium have been deposited, possibly supplemented with iridium; a Y-type zeolite having undergone activation treatment. Most preferred is silica-alumina.

When a metal oxide alone or a metal oxide in combination with other metals or metalloid oxides or a metal oxide having one or more noble metals (Pt, Pd, Rh, Ru, Os, Ir) deposited on its surface, an atmosphere of hydrogen is generally selected in order to prolong catalytic activity. In any case, the catalyst can be used in a fluid bed or fixed bed. The specific surface area of the catalyst useful according to this invention can range between 0.1 and 600 $m^2/g$.

Suitable solvents for 3,5,5-trimethyl-2-cyclohexene-1,4-dione include solvents which are inert to the reactant at reaction conditions and include aromatic hydrocarbons, e.g., benzene and toluene; aliphatic and cycloaliphatique hydrocarbons, e.g. hexane and cyclohexane.

A preferred embodiment of the process of this invention comprises charging the tubular reactor with an alumina-silica catalyst, calcining the catalyst in air, purging the reaction with nitrogen, adjusting the reactor to reaction temperature, injecting hydrogen and a solution of 3,5,5-trimethyl-2-cyclohexene-1,4-dione in benzene, totally vaporizing the 3,5,5-trimethyl-2-cyclohexene-1,4-dione, mixing the vaporized 3,5,5-trimethyl-2-cyclohexene-1,4-dione with hydrogen, forming a gaseous mixture therefrom and contacting the gaseous mixture with the alumina-silica catalyst.

At the end of the reaction, the presence of a small quantity of trimethyl-p-benzoquinone can be observed along with the trimethylhydroquinone. The trimethyl-p-benzoquinone is formed from the trimethylhydroquinone, and occurs either from the oxidation during the reaction or after the reaction upon contact with air. It may easily be reduced by known means, e.g., treatment with zinc.

The following examples illustrate the process of the invention and are not to be taken as limiting in any sense.

EXAMPLE 1

In a tubular glass reactor (length, 9 cm; diameter 1.25 cm) placed vertically in an annular electric oven, 3.13 g. are charged with a catalyst containing by weight 87% silica and 13% alumina and having a specific surface of 97 $m^2/g$ (GRACE DAVISON Chemical SMR 7.2213) to form a fixed bed. The catalyst is calcinated in air at 500° C. for four hours. Then the reactor is purged with nitrogen, and 17l/h of dry hydrogen and 6.3 $cm^3/h$ of a solution of 52.6 g of 3,5,5-trimethyl-2-cyclohexene-1,4-dione in a quantity of benzene sufficient to obtain a total solution volume of 100 $cm^3$ are injected into the reaction zone. The catalytic bed maintained at 450° C. is contacted with the gaseous mixture. After the reaction is complete, the reaction products are collected from the reaction mixture by condensation in a series of traps cooled by an acetone-carbonic ice mixture. After four hours of continuous operation, the reaction is halted. The contents of the traps are collected into a single fraction and are mixed with a sufficient quantity of acetone to obtain a total volume of 50 $cm^3$. The unreacted 3,5,5-trimethyl-2-cyclohexene-1,4-dione is determined directly into the acetone solution obtained above. This acetone solution is subjected to gas-phase chromatographic analysis ans it was determined that 8.9 g. of 3,5,5-trimethyl-2-cyclohexene-1,4-dione are present, which corresponds to a conversion rate of 32.9%. The trimethylhydroquinone formed is determined by polarography after reducing, by zinc, the small amount of trimethyl-p-benzoquinone present alongside the trimethylhydroquinone; 2.15 g. of trimethylhydroquinone are thus found, corresponding to a yield of 49.9% of the starting material, 3,5,5-trimethyl-2-cyclohexene-1,4-dione. The trimethylhydroquinone in acetone solution is distilled under atmospheric pressure. After the acetone is removed by distillation, 40 $cm^3$ of boiling hexane are added. After cooling, the trimethylhydroquinone is separated from the hexane by filtration. For further purification the product is recrystallized in 30 $cm^3$ of toluene, and is filtered, resulting in 1.56 g. of trimethylhydroquinone.

The following analysis are carried out on the trimethylhydroquinone product:
polargraphic determination: 96.6%
melting point: 169° C.
mass spectrum: conforms to theory

EXAMPLE 2

In a rector such as described in Example 1, 2.89 g. of the same catalyst are charged and calcinated for three hours at 500° C. Then 18l/h of hydrogen and 12.4 $cm^3$ of a solution of 27 g. of 3,5,5-trimethyl-2-cyclohexene-1,4-dione in a quantity of benzene sufficient to obtain a total solution volume of 100 $cm^3$ are injected. After 29 minutes of reaction time, gas-phase chromatography methods are used to titrate 1.16 g. of unreacted 3,5,5-trimethyl-2-cyclohexene-1,4-dione, for a conversion rate of 28.4%. After reduction by zinc, polarography is used to titrate 0.253 g. of trimethylhydroquinone; the yield of converted 3,5,5-trimethyl-2-cyclohexene-1,4-dione is 52.8%.

EXAMPLE 3

In a reactor such as described in Example 1, 1.482 g. of a Y-type zeolite are charged, and in which the $Na^+$ ions have been almost totally exchanged for $NH_4^+$ ions.

The crystals have the following structure: 2 Na$^+$, 54 NH$_4^+$, 136 SiO$_2$, 28 Al$_2$O$_3$.

The zeolite is calcinated in a current of air by progressively raising the temperature from 25° C. to 500° C. over a period of five hours, then it is maintained at 450° C. for 15 hours. The temperature in the reaction zone is maintained at 450° C. and 10 l/h of hydrogen and 12.6 cm$^3$/h of a solution of 25 g. of 3,5,5-trimethyl-2-cyclohexene-1,4-dione in a quantity of benzene sufficient to obtain a volume of 100 cm$^3$ is injected. After 30 minutes of reaction time, 1.575 g. of 3,5,5-trimethyl-2-cyclohexene-1,4-dione have been injected and gas-phase chromatography gives 1.205 g. of unreacted dione, corresponding to a transformation rate of 23.5%. After reduction by zinc, 0.183 g. of trimethylhydroquinone is titrated; the yield of transformed 3,5,5-trimethyl-2-cyclohexene-1,4-dione is 49.5%.

What is claimed is:

1. A process for the preparation of trimethylhydroquinone which comprises conjointly isomerizing, aromatizing and reducing 3,5,5-trimethyl-2-cyclohexene-1,4-dione in the vapor phase with an acid catalyst at a reaction temperature between 200° and 600° C., wherein said acid catalyst is selected from the group consisting of metal oxides of Group IIa, IIb, IIIa, IIIb, IVb, Vb, VIIb and VIII of the Periodic Table of Elements, and metal oxides mixed with metalloid oxides, natural alumina silicates, natural zeolites and synthetic zeolites and mixtures thereof.

2. The process according to claim 1, wherein said acid catalyst comprises metal oxides of Group IIa, IIb, IIIa, IIIb, IVb, Vb, VIIb, and VIII of the Periodic Table of Elements.

3. The process according to claim 2, wherein said acid catalyst is selected from the group consisting of alumina, alumina mixed with a metal oxide of Group IIa, IIb, IIIa, IIIb, IVb, Vb, VIIb, and VIII of the Periodic Table of Elements, and alumina mixed with a metalloid oxide.

4. The process according to claim 1, wherein noble metals of Group VIII of the Periodic Table of Elements are deposited on said acid catalyst.

5. The process according to claim 2, wherein said acid catalyst is subjected to acid treatment.

6. The process according to claim 3, wherein said acid catalyst is subjected to acid treatment.

7. The process according to claim 3, wherein said acid catalyst is silica-alumina.

8. The process according to claim 1, wherein the reaction is carried out in an atmosphere of inert gas or hydrogen.

* * * * *